United States Patent [19]

Onopchenko et al.

[11] 4,009,211
[45] Feb. 22, 1977

[54] BETA,BETA-DIALKYLETHYLMERCAPTO-ETHOXYLATE AS NEW COMPOUNDS

[75] Inventors: Anatoli Onopchenko, Monroeville; Johann G. D. Schulz, Pittsburgh, both of Pa.

[73] Assignee: Gulf Research & Development Company, Pittsburgh, Pa.

[22] Filed: July 29, 1975

[21] Appl. No.: 600,150

[52] U.S. Cl. .......................... 260/609 R; 252/530; 252/532; 252/549
[51] Int. Cl.² ....................................... C07C 149/18
[58] Field of Search ................... 260/609 R

[56] References Cited

UNITED STATES PATENTS

| | | | |
|---|---|---|---|
| 2,494,610 | 1/1950 | Davidson et al. | 260/609 R |
| 2,565,986 | 8/1951 | Olin | 260/609 R |
| 2,619,466 | 11/1952 | Wolf | 260/609 A |

*Primary Examiner*—Lewis Gotts
*Assistant Examiner*—D. R. Phillips

[57] ABSTRACT

Beta,beta-dialkylethylmercaptoethoxylate as new compounds.

2 Claims, No Drawings

BETA,BETA-DIALKYLETHYLMERCAPTOE-THOXYLATE AS NEW COMPOUNDS

BACKGROUND OF THE INVENTION

1. Field of the Invention

This invention relates to beta,beta-dialkylethylmercaptoethoxylate as new compounds that are surprisingly fluid at room temperature and possess improved detergency properties.

2. Description of the Prior Art

Many effective detergents have been prepared using normal alpha olefins as a component thereof. In the preparation of normal alpha olefin using the Ziegler process wherein ethylene is oligomerized in the presence of an aluminum alkyl, vinylidene olefins are also obtained as a by-product. The composition defined and claimed herein can utilize such vinylidene olefin as a component thereof.

SUMMARY OF THE INVENTION

The beta,beta-dialkylethylmercaptoethoxylates defined and claimed herein can be described by reference to the following structural formula:

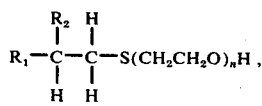

wherein $R_1$ and $R_2$, the same or different, are alkyl substituents having from one to ten carbon atoms, preferably from two to six carbon atoms, such as methyl, ethyl, propyl, n-butyl, n-pentyl, isopropyl, isobutyl, 4-methylhexyl, 5-ethyloctyl, 3,6-dimethyloctyl, etc., wherein the number of carbon atoms in $R_1 + R_2$ is in the range of three to 20, preferably eight to 16, and n is an integer from 8 to 26, preferably from 8 to 16.

Among the specific compounds that are included in the above structural formula are:
2-methylpentylmercaptotriethoxy ethoxylate
2-methylhexylmercaptotriethoxy ethoxylate
2-methylheptylmercaptotriethoxy ethoxylate
2-methyloctylmercaptotriethoxy ethoxylate
2-methylnonylmercaptotriethoxy ethoxylate
2-methyldecylmercaptotriethoxy ethoxylate
2-methyldodecylmercaptotriethoxy ethoxylate
2-ethylbutylmercaptotriethoxy ethoxylate
2-ethylpentylmercaptotriethoxy ethoxylate
2-ethylhexylmercaptotriethoxy ethoxylate
2-ethylheptylmercaptotriethoxy ethoxylate
2-ethyloctylmercaptotriethoxy ethoxylate
2-ethylnonylmercaptotriethoxy ethoxylate
2-ethyldecylmercaptotriethoxy ethoxylate
2-propylbutylmercaptotriethoxy ethoxylate
2-propylpentylmercaptotriethoxy ethoxylate
2-propylhexylmercaptotriethoxy ethoxylate
2-propylheptylmercaptotriethoxy ethoxylate
2-propyloctylmercaptotriethoxy ethoxylate
2-propylnonylmercaptotriethoxy ethoxylate
2-propyldecylmercaptotriethoxy ethoxylate
2-propyldodecylmercaptotriethoxy ethoxylate
2-butylhexylmercaptotriethoxy ethoxylate
2-butylheptylmercaptotriethoxy ethoxylate
2-butyloctylmercaptotriethoxy ethoxylate
2-butylnonylmercaptotriethoxy ethoxylate
2-butyldecylmercaptotriethoxy ethoxylate
2-butyldodecylmercaptotriethoxy ethoxylate, etc.,
the corresponding tetra-, penta-, hexa-, hepta-, octa-, nona-, deca-, undeca-, dodeca-, trideca-, tetradeca-, pentadeca-, hexadeca-, octadeca-, eicosano-, tetraeicosano-, hexaeicosano-, etc., ethoxylates, etc.

The novel compounds defined and claimed herein can be prepared by reacting a specific vinylidene olefin, defined hereinafter, with mercaptoethanol to form the corresponding thioetherethanol adduct and then reacting the adduct so formed with ethylene oxide to obtain the beta,beta-dialkylethylmercaptoethoxylate.

In the reaction between the vinylidene olefin and the mercaptoethanol, the vinylidene olefin that is used can be defined by reference to the following structural formula:

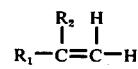

wherein $R_1$ and $R_2$, the same or different, are alkyl substituents as defined above, with the number of carbon atoms in $R_1 + R_2$ also as defined above. Specific examples of vinylidene olefins that can be used include:
2-methyl-1-octene
2-methyl-1-nonene
2-methyl-1-decene
2-methyl-1-undecene
2-methyl-1-dodecene
2-ethyl-1-octene
2-ethyl-1-nonene
2-ethyl-1-decene
2-ethyl-1-undecene
2-ethyl-1-dodecene
2-ethyl-1-tetradecene
2-ethyl-1-hexadecene
2-ethyl-1-octadecene
2-propyl-1-hexene
2-propyl-1-heptene
2-propyl-1-octene
2-propyl-1-nonene
2-propyl-1-decene
2-propyl-1-dodecene
2-butyl-1-butene
2-butyl-1-pentene
2-butyl-1-hexene
2-butyl-1-heptene
2-butyl-1-octene
2-butyl-1-decene
2-butyl-1-dodecene
2-pentyl-1-octene
2-pentyl-1-nonene
2-pentyl-1-decene
2-pentyl-1-undecene
2-pentyl-1-dodecene
2-hexyl-1-pentene
2-hexyl-1-hexene
2-hexyl-1-heptene
2-hexyl-1-octene
2-hexyl-1-nonene
2-hexyl-1-dodecene, etc., mixtures of the above, etc.

In forming the adduct the vinylidene olefin and the mercaptoethanol are brought together and, while stirring, are maintained at a temperature of about 0° to about 150° C., or even higher, preferably about 26° to about 100° C., and a pressure of about 14.7 to about 300 pounds per square inch gauge (about 1.0 to about 21 kilograms per square centimeter), preferably about 14.7 to about 75 pounds per square inch gauge (about 1.0 to about 5.3 kilograms per square centimeter), for about one minute to about 48 hours, preferably about 10 minutes to about 6 hours.

Solvents are not needed for adduct formation, although solvents, such as methanol, ethanol, benzene, carbon tetrachloride, chloroform, carbon disulfide, etc., can be used, if desired, for example, to help solubilize solid olefins used. Initiators are not needed, although, if desired, such well-known initiators as azobisisobutyronitrile, hydrogen peroxide, tert-butyl hydroperoxide, dibutyl peroxide, cumene hydroperoxide, ultraviolet light, ozone, etc., can be used.

For adduct formation equal molar amounts of reactant olefin and mercaptoethanol are theoretically required. In practice, excess amounts of one of the reactants are used. With lower vinylidene olefin reactant, for example $C_8$ to $C_{10}$ olefins, excess olefin is used, since the excess olefin can readily be removed from the adduct product by flash evaporation. With higher olefins, for example, $C_{10}$ and above excess mercaptoethanol is used, because the excess mercaptoethanol can be removed easily from the adduct formed merely by washing the same with water.

The adduct so obtained is then reacted with ethylene oxide. This can be done, for example, by adding ethylene oxide to a stirred mixture of adduct containing from about 0.05 to about 5.0 grams, preferably about 0.1 to about 0.5 grams per gram of adduct, of a catalyst, such as sodium or potassium hydroxide or sodium or potassium metal, while maintaining the reaction mixture within a temperature range of about 120° to about 200° C., preferably about 120° to about 150° C., and a pressure of about 14.7 to about 150 pounds per square inch gauge (about 1.0 to about 10.5 kilograms per square centimeter), preferably about 14.7 to about 50 pounds per square inch qauge (about 1.0 to about 3.5 kilograms per square centimeter) for about 5 minutes to about 10 hours, preferably about 10 minutes to about 2 hours. The beta,beta-dialkylethylmercaptoethoxylate product obtained will be a mixture of individual beta,beta-dialkylethylmercaptoethoxylates wherein the number of ethoxylate units introduced into the adduct will depend on the amount of ethylene oxide used and the reaction conditions employed. In general, at least about three mols of ethylene oxide, preferably about five to about 15 mols of ethylene oxide, most preferably about eight to about 12 mols of ethylene oxide, will be sufficient to obtain a product containing ethoxylate groups sufficient to satisfy the requirements of the structural formula of the new beta,beta-dialkylethylmercaptoethoxylate claimed herein, as well as to give a completely miscible product.

DESCRIPTION OF PREFERRED EMBODIMENTS

The invention defined herein can further be illustrated by the following.

EXAMPLE I

A stirred mixture of 84 grams of 1-dodecene and 45 grams of 2-mercaptoethanol were reacted at a temperature of 26° C. over a period of 48 hours. The reaction product amounted to 116 grams, or a 94 weight percent yield of the adduct, normal dodecyl, 2-hydroxyethyl, thioether (n - $C_{12}H_{25}$ - S - $CH_2CH_2OH$).

EXAMPLE II

The run of Example I was repeated using 32.6 grams of 1-tetradecene and 13.0 grams of 2-mercaptoethanol. The reaction product obtained amounted to 43 grams, or a 95 weight percent yield of the adduct normal tetradecyl, 2-hydroxyethyl, thioether (n - $C_{14}H_{29}$ - S - $CH_2CH_2OH$).

EXAMPLE III

The run of Example I was again repeated using 112 grams of 1-hexadecene and 45 grams of 2-mercaptoethanol. The reaction product obtained amounted to 143 grams, or a 95 weight percent yield of the adduct normal hexadecyl, 2-hydroxyethyl, thioether (n - $C_{16}H_{33}$ - S - $CH_2CH_2OH$).

EXAMPLE IV

In this run when the run of Example I was repeated 42 grams of Jefferson $C_{12}$ dimer olefin was reacted with 21 grams of 2-mercaptoethanol. The reaction product obtained amounted to 57 grams, or a 92 weight percent yield of the adduct

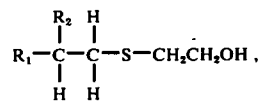

wherein each of $R_1$ and $R_2$ was an alkyl group, with the total number of carbon atoms in $R_1 + R_2$ being 10. The adduct had a refractive index $n_D^{28}$ of 1.4710.

EXAMPLE V

Repeating Example IV with 200 grams of Jefferson $C_{14}$ dimer olefin and 105 grams of 2-mercaptoethanol resulted in the production of 263 grams of product, or a 94 weight percent yield of the adduct

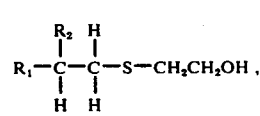

wherein each of $R_1$ and $R_2$ was an alkyl group, with the total number of carbon atoms in $R_1 + R_2$ being 12. The adduct had a refractive index $n_D^{28}$ of 1.4710.

EXAMPLE VI

In this run, Example IV was repeated using 50 grams of Jefferson $C_{16}$ dimer olefin and 19 grams of 2-mercaptoethanol. There was obtained 61 grams of product or a 91 weight percent yield of the adduct

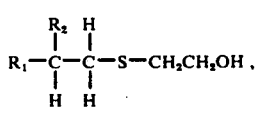

wherein each of $R_1$ and $R_2$ was an alkyl group, with the total number of carbon atoms in $R_1 + R_2$ being 14. The adduct had a refractive index $n_D^{28}$ of 1.4629.

EXAMPLE VII

When the run of Example IV was repeated using 52 grams of Jefferson $C_{18}$ dimer and 18 grams of 2-mercaptoethanol, there was obtained 63 grams of product, or a 92 weight percent yield of the adduct

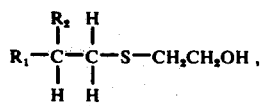

wherein each of $R_1$ and $R_2$ was an alkyl group, with the total number of carbon atoms in $R_1 + R_2$ being 16. The adduct had a refractive index $n_D^{28}$ of 1.4670.

Each of the dimer olefins used in Examples IV, V, VI and VII are vinylidene olefins manufactured and sold by the Jefferson Chemical Company having the following structural formula:

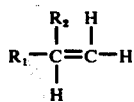

Analysis of the olefins by NMR showed $R_1$ and $R_2$ in each dimer olefin to be an alkyl group larger than methyl group, with the total number of carbon atoms in $R_1 + R_2$ in each of the dimer olefins used in Examples IV, V, VI and VII being 10, 12, 14 and 16, respectively.

Each of the adducts prepared in Examples I, II and III in which an alpha olefin was used in its preparation was a solid, whereas, surprisingly, each of the adducts prepared in Examples IV, V, VI and VII, wherein a vinylidene or dimer olefin, was used in its preparation, was a fluid.

A series of runs was made wherein the adduct prepared in each of Examples I to VII above was ethoxylated with ethylene oxide. This was done by placing the adduct in a flask, the flask was then purged with nitrogen and 0.2 gram of sodium metal was added thereto. With the nitrogen purge on, the reaction mixture was heated while maintaining atmospheric pressure, and, while being stirred, ethylene oxide was added thereto through a sparger. Addition of ethylene oxide was continued for about 5.5 hours or until the desired amount of ethylene oxide had been added, after which the mixture was cooled to room temperature and the caustic therein neutralized with phosphoric acid until the final solution was neutral toward litmus paper. While the minimum and the maximum amount of ethylene oxide required to give a completely water miscible product were not determined for each vinylidene olefin reacted, the total ethylene oxide content of around 65 weight percent was sufficient for $C_{12-18}$ olefin derived products to have good solubility properties in water. The resulting product was a mixture of alkylethylmercaptoethoxylates made up of individual alkylethylmercaptoethoxylates wherein at least one ethylene oxide unit and in most cases a much larger number of ethylene oxide units had been introduced into the adduct charge molecule. The alkylethylmercaptoethoxylates obtained were analyzed to determine the average number of ethylene oxide units in the alkylethylmercaptoethoxylate product and the average molecular weight thereof. The results of these runs are summarized in Table I below.

TABLE I

| Example | Source of Adduct | Grams of Adduct | Ethylene Oxide, Grams | Ethoxylation Temperature, °C. | Total Ethylene Oxide Content Of Ethoxylated Product, Weight Per Cent | Product R—S—(CH₂CH₂O)ₙH Average Molecular Weight | n, Average | Remarks Concerning Ethoxylates |
|---|---|---|---|---|---|---|---|---|
| VIII | Example I | 60.5 | 83.7 | 140–150 | 65.5 | 633 | 8.8 | Semi Solid |
| IX | Example II | 33.5 | 46.0 | 140–150 | 64.8 | 701 | 9.7 | Solid Wax |
| X | Example III | 60.5 | 82.4 | 140–150 | 63.8 | 755 | 10.3 | Solid Wax |
| XI | Example IV | 50.0 | 69.0 | 140–150 | 65.4 | 629 | 8.7 | Fluid |
| XII | Example V | 60.3 | 76.3 | 140–150 | 63.0 | 701 | 9.7 | Fluid |
| XIII | Example VI | 54.0 | 68.0 | 140–150 | 62.0 | 724 | 9.6 | Fluid |
| XIV | Example VII | 55.0 | 76.1 | 140–150 | 63.7 | 827 | 11.3 | Fluid |

The alkyl substituents in the ethoxylates obtained in each of VIII, IX, X, XI, XII, XIII and XIV correspond to the alkyl substituents in the adducts of Examples I, II, III, IV, V, VI and VII, respectively. By "total ethylene oxide content" of ethoxylated product we mean to include the total CH₂CH₂O- units in the final product. The total ethylene oxide content can be calculated from the following expression:

$$\text{Total Ethylene Oxide Content} = \frac{\text{Weight In Grams of ethylene Oxide Added} + \text{Weight In Grams Of Adduct Added} \cdot \frac{44}{\text{Molecular Weight Of Adduct}}}{\text{Weight in grams Of Ethylene Oxide Added} + \text{Weight In Grams Of Adduct}} \times 100$$

Note that while the ethoxylates prepared from alpha olefins are solids, unexpectedly those prepared using vinylidene olefins are fluid. The latter characteristic is desirable, since it facilitates handling and transferring of the compounds and renders them attractive in compounding formulations containing the same.

Each of the ethoxylates produced in Examples IX and XII above was tested for its detergency characteristics. Also tested was an ethoxylate produced from Shell Chemical Company's Neodol 25-9 (a mixture of $C_{12}$ to $C_{15}$ normal straight chain alcohols). This ethoxylate was prepared by reacting the alcohol mixture with ethylene oxide at atmospheric pressure and a temperature of 140° to 150° C. in a nitrogen atmosphere until the average ethoxylate had an average total of 8.3 CH₂CH₂O- groups, constituting about 65 weight percent of the molecule. The data obtained are set forth in Table II below. In the table, the Canvas-Square method involves placing one-inch squares of No. 6 canvas on the surface of a solution of distilled water containing defined weight percent of the detergent in question and determining the amount of time required for the canvas squares to sink below the surface. (Procedure of S. Edelstein et al, *Amer. Dyestuff Reporter*, Apr. 18, 1949, pages 343 to 347)

The results in Table III above indicate good fabric cleansing for the ethoxylated products obtained from the olefins, at least comparable to the ethoxylated alco-

TABLE II

| | Ethoxylate Of $C_{14}$ Vinylidene Thioglycol | Ethoxylate Of $C_{14}$ Alpha Olefin Thioglycol | Ethoxylate Of Shell $C_{12}$–$C_{15}$ Alcohol |
|---|---|---|---|
| Cloud Point, °C. of 1.0 Weight Per Cent Solution (ASTM D-2024) | 32 | 64 | 64 |
| Surface Tension, Dynes Per Centimeter At 25° C. (ASTM D-1331) | | | |
| 1.0 Weight Per Cent | 30 | 34 | 29 |
| 0.1 Weight Per Cent | 30 | 35 | 29 |
| 0.01 Weight Per Cent | 31 | 35 | 31 |
| 0.001 Weight Per Cent | 33 | 40 | 39 |
| Interfacial Tension Against Mineral Oil Dynes Per Centimeter At 25° C. (ASTM D-1331) | | | |
| 1.0 Weight Per Cent | 6 | 7 | 2 |
| 0.1 Weight Per Cent | 7 | 9 | 4 |
| 0.01 Weight Per Cent | 11 | 12 | 7 |
| 0.001 Weight Per Cent | 16 | 18 | 16 |
| Wetting By Canvas-Square Method, Seconds At 25° C. In Distilled Water | | | |
| 0.2 Weight Per Cent | 33 | >120 | — |
| 0.1 Weight Per Cent | 47 | >120 | — |
| 0.05 Weight Per Cent | 74 | >120 | — |
| Foaming By Ross-Miles Method, Centimeter, Initial After Five Minutes At 49° C. (ASTM D-1173) Distilled Water | | | |
| 0.1 Weight Per Cent | 3.0/2.5 | 5.5/3.5 | 9.5/9.5 |
| 0.05 Weight Per Cent | 2.0/2.0 | 4.0/3.0 | 7.0/7.0 |
| Soft Water (50 Parts Per Million) | | | |
| 0.1 Weight Per Cent | 2.0/1.5 | 5.0/3.0 | 8.5/8.5 |
| 0.05 Weight Per Cent | 1.5/1.0 | 4.0/3.0 | 7.0/7.0 |
| Hard Water (150 Parts Per Million) | | | |
| 0.1 Weight Per Cent | 2.0/1.5 | 5.0/3.5 | 8.0/8.0 |
| 0.05 Weight Per Cent | 2.0/1.5 | 3.5/2.0 | 6.0/5.5 |
| Lime Soap Dispersion (Weight Per Cent Required To Disperse 100 Grams of Calcium-Magnesium Oleate) | 5 | 5 | 5 |

Note in the data of Table II above that the vinylidene ethoxylate, claimed herein, has a much lower cloud point than the other ethoxylates. The surface and interfacial tension of the vinylidene ethoxylates is typical for a nonionic surfactant and comparable to those of the other two nonionic surfactants. Its wetting power was, however, superior to the wetting power of the normal alpha olefin-derived ethoxylate. The wetting characteristics of the ethoxylate obtained from the mixture of alcohol was not determined. Foaming of the vinylidene derived ethoxylate was also superior to that of the remaining ethoxylates. Lime soap dispersion tests were conducted on each of the above detergents and in each case was found to be identical.

Each of the above surfactants was tested for its detergency properties on cotton and polyester fabrics using the conventional procedure described by W. G. Spangler et. al., *J. Amer. Oil Chem. Soc.*, 42 (8) 724 (1965), with the reflectance being read on a Hunter Model D 25 Apparatus. The results obtained are tabulated below in Table III.

hol. All were equivalent on cotton, while greater efficiencies were observed on polyester. Since polyester is particularly difficult to cleanse, this appears to be a significantly desirable property in a surfactant.

Obviously, many modifications and variations of the invention, as hereinabove set forth, can be made without departing from the spirit and scope thereof, and therefore only such limitations should be imposed as are indicated in the appended claims.

We claim:
1. Novel beta,beta-dialkylethylmercaptoethoxylates of the following structural formula:

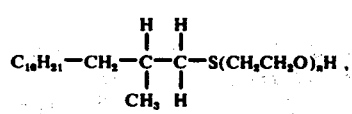

wherein $n$ is an integer from 8 to 16.
2. The compound of claim 1 wherein $n$ is 9.7.

* * * * *

TABLE III

| | $R_d(b)$ Reflectance After Three Soil Washings[2] | | | |
|---|---|---|---|---|
| Active Ingredient[1] | Cotton | | Polyester | |
| (Thioglycol Ethoxylate Derived From) | Wash | Redeposition | Wash | Redeposition |
| $C_{14}$ Vinylidene Olefin | 80.3(2.8) | 87.8(1.0) | 76.7(4.2) | 85.9(0.9) |
| $C_{14}$ Normal Alpha Olefin | 90.7(2.6) | 88.0(1.0) | 70.4(4.6) | 84.6(1.3) |
| Mixture Of $C_{12}$ To $C_{15}$ Normal Alcohols (Neodol 25-9, A typical nonionic detergent) | 80.9(2.6) | 88.4(0.9) | 68.8(4.8) | 83.6(1.5) |

[1]Detergent formulation: 15 weight per cent nonionic ethoxylate, 35 weight per cent sodium tripolyphosphate, 8 weight per cent sodium silicate and 42 weight per cent sodium sulfate.
[2]Washing done in Terg-O-Tometer at 100 cycles per minute for 10 minutes at 49° C. with water at 125 parts per million hardness, detergent concentration = 0.15 weight per cent and rinsed three minutes under same conditions.